United States Patent
Lee et al.

(10) Patent No.: US 10,206,987 B2
(45) Date of Patent: Feb. 19, 2019

(54) PROTEIN NANOPARTICLE LINKED WITH CANCER SPECIFIC EPITOPE AND COMPOSITION FOR CANCER IMMUNOTHERAPY COMPRISING THE SAME

(71) Applicants: Korea University Research And Business Foundation, Seoul (KR); Korea Institute of Science and Technology, Seoul (KR)

(72) Inventors: Jeewon Lee, Seoul (KR); Bo Ram Lee, Seoul (KR); Kwangmeyung Kim, Seoul (KR); Ju Hee Ryu, Seoul (KR); Ho Kyung Ko, Seoul (KR)

(73) Assignees: KOREA UNIVERSITY RESEARCH AND BUSINESS FOUNDATION, Seoul (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/299,993

(22) Filed: Oct. 21, 2016

(65) Prior Publication Data

US 2017/0112910 A1    Apr. 27, 2017

(30) Foreign Application Priority Data

Oct. 22, 2015 (KR) ........................ 10-2015-0147592

(51) Int. Cl.
| | | |
|---|---|---|
| A61K 39/00 | (2006.01) | |
| A61K 9/14 | (2006.01) | |
| B82Y 5/00 | (2011.01) | |

(52) U.S. Cl.
CPC ............ *A61K 39/0011* (2013.01); *A61K 9/14* (2013.01); *A61K 2039/55555* (2013.01); *A61K 2039/6031* (2013.01); *B82Y 5/00* (2013.01)

(58) Field of Classification Search
CPC ....... A61K 39/0011; A61K 39/00; A61K 9/14
USPC ........................................................ 435/325
See application file for complete search history.

(56) References Cited

FOREIGN PATENT DOCUMENTS

WO    WO 2015/135597    * 9/2015

OTHER PUBLICATIONS

Harrison, P., et al., "The Ferritins: Molecular Properties, Iron Storage Function and Cellular Regulation", "Biochimica et Biophysica Acta", Feb. 27, 1996, pp. 161-203, vol. 1275, Publisher: Elsevier Science B.V.

Jewell, C., et al., "In Situ Engineering of the Lymph Node Microenvironment via Intranodal Injection of Adjuvant-Releasing Polymer Particles", "Proceedings of the National Academy of Sciences", Sep. 20, 2011, pp. 15745-15750, vol. 108, No. 38.

Lawson, D., et al., "Solving the Structure of Human H Ferritin by Genetically Engineering Intermolecular Crystal Contacts", "Letters to Nature", Feb. 7, 1991, pp. 541-544, vol. 349, Publisher: Nature Publishing Group.

Lee, B., "Engineering of Protenticle for in vivo LN Detection and Cancer Immunotherapy", "CHERIC: Chemical Engineering and Materials Research Information Center", Oct. 23, 2014.

Xu, Z., et al., "Multifunctional Nanoparticies Co-Delivering Trp2 Peptide and CpG Adjuvant Induce Potent Cytotoxic T-lymphocyte Response Against Melanoma and its Lung Metastasis", "Journal of Controlled Release", Sep. 1, 2013, pp. 259-265, vol. 172, Publisher: Elsevier B.V.

* cited by examiner

*Primary Examiner* — Yan Xiao
(74) *Attorney, Agent, or Firm* — Hultquist, PLLC; Steven J. Hultquist

(57) ABSTRACT

The present invention relates to a protein nanoparticle having a surface on which a cancer-specific epitope is fused and expressed, a method for producing the same, and a composition for cancer immunotherapy containing the protein nanoparticle as an active ingredient, and more specifically, to a recombinant microorganism into which a vector in which a promoter, a gene of a human ferritin heavy chain protein, and a gene encoding the cancer-specific epitope are operably linked is introduced, a protein nanoparticle in which a cancer-specific epitope is fused and expressed on a surface of the human ferritin heavy chain protein, a method of producing the protein nanoparticle, and a composition for cancer immunotherapy including the protein nanoparticle as the active ingredient, wherein the cancer-specific epitope on the surface of the protein nanoparticle according to the present invention is able to be expressed with correct orientation and high density, and the composition for cancer immunotherapy including the protein nanoparticle as the active ingredient has significantly excellent cancer immunotherapeutic effect as compared to the existing nanoparticle-based composition.

9 Claims, 10 Drawing Sheets

Specification includes a Sequence Listing.

[FIG 1]
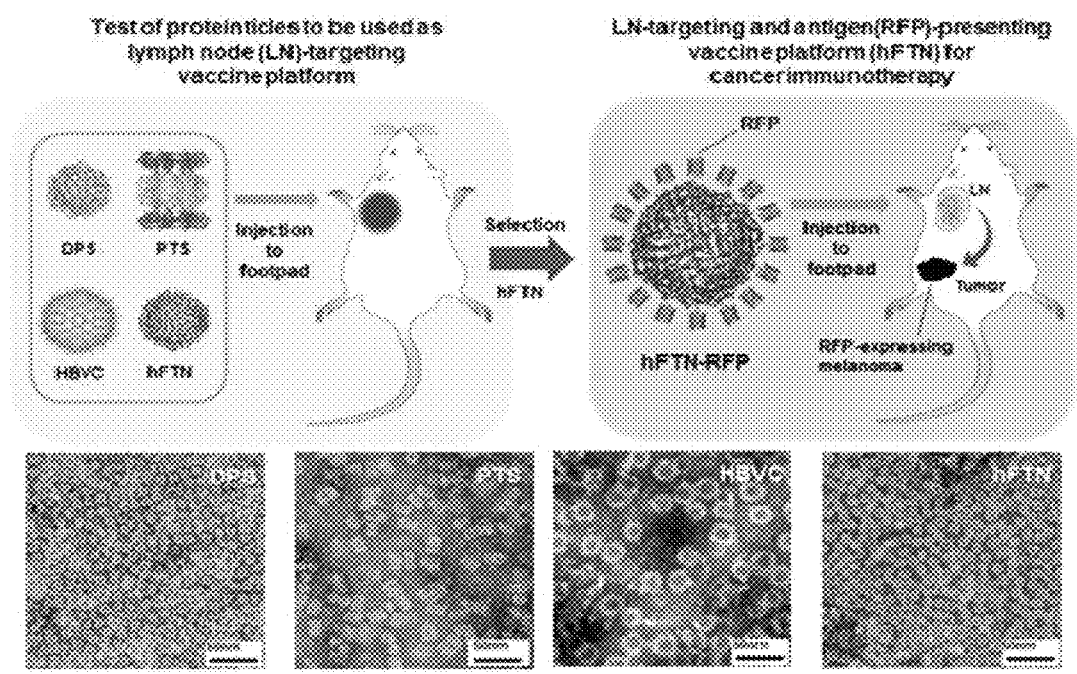
[FIG 2]
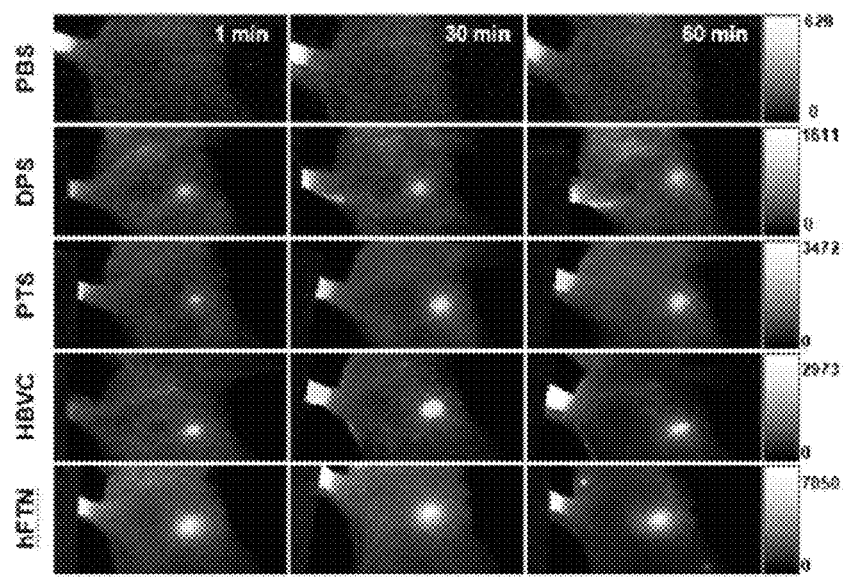

[FIG 3A]
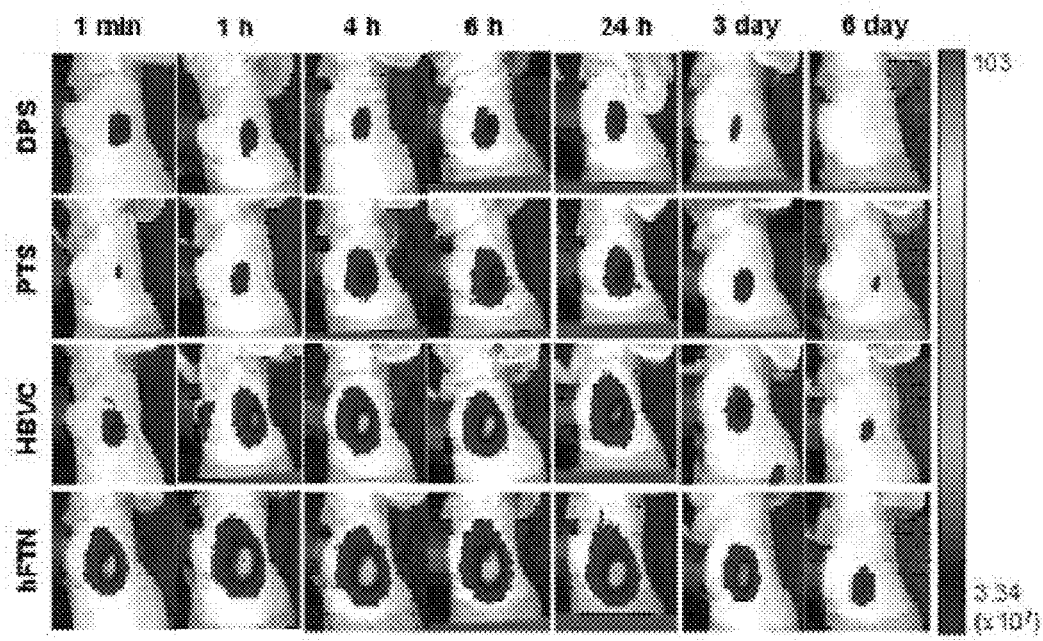
[FIG 3B]
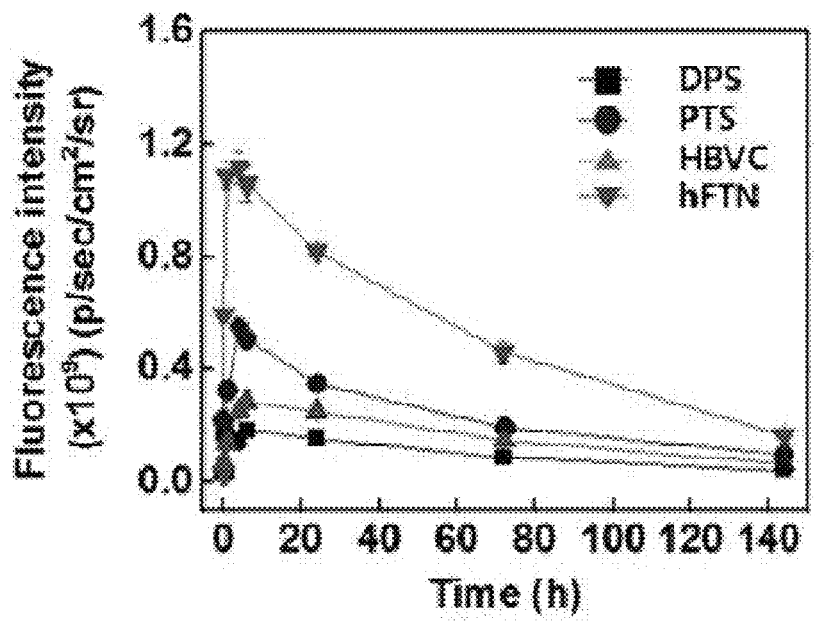

[FIG 4A]
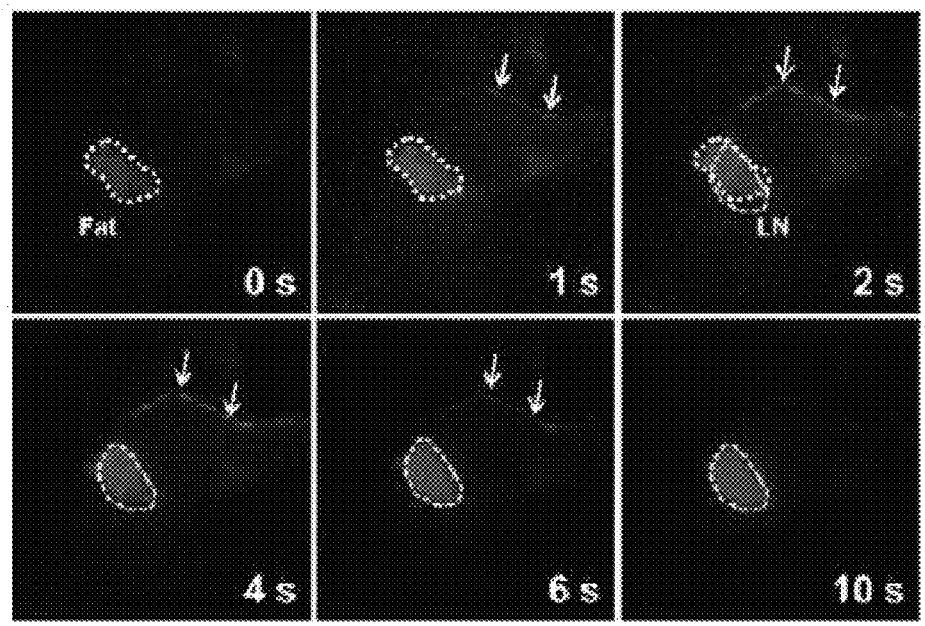
[FIG 4B]
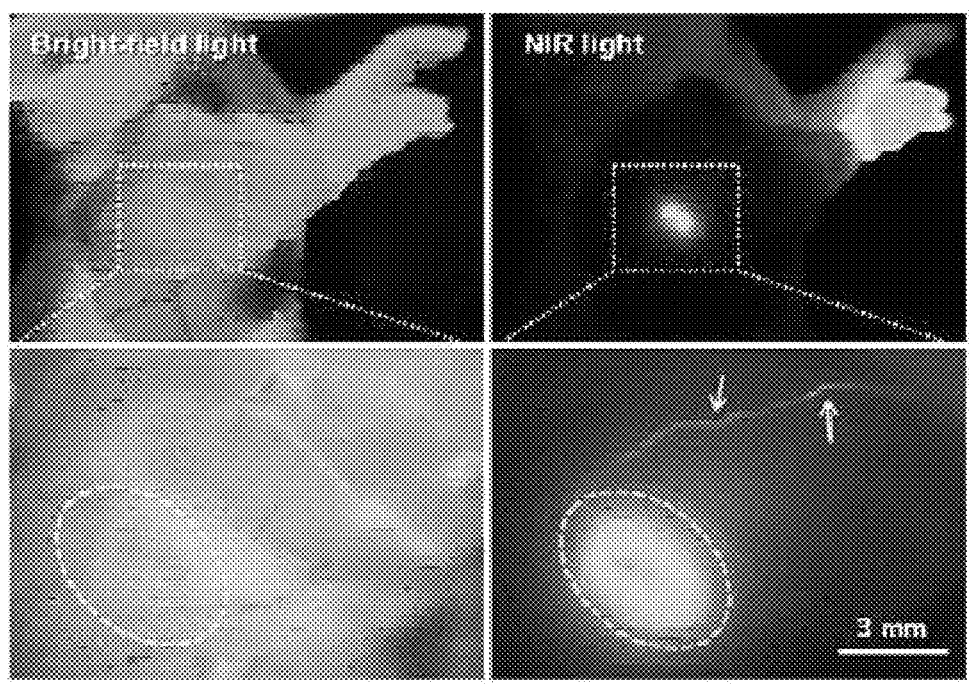

[FIG 5A]
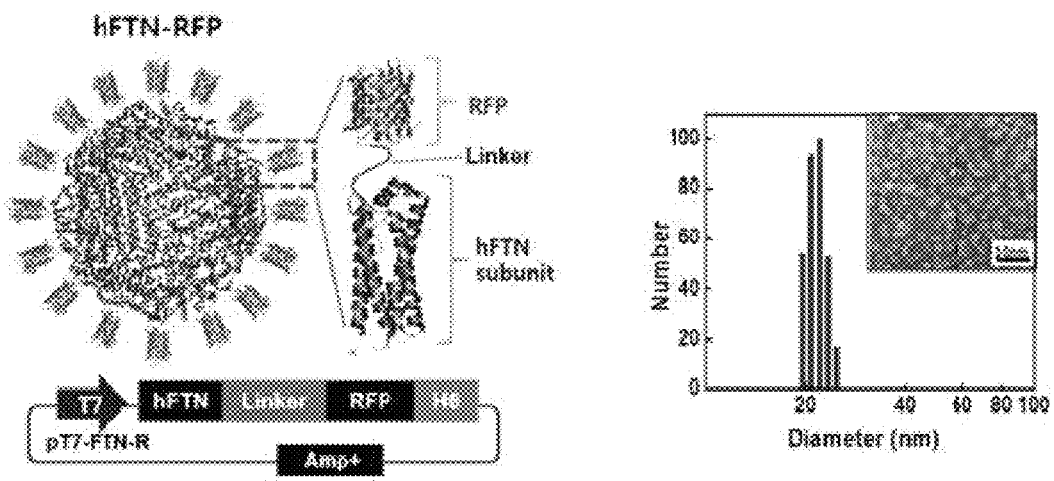
[FIG 5B]
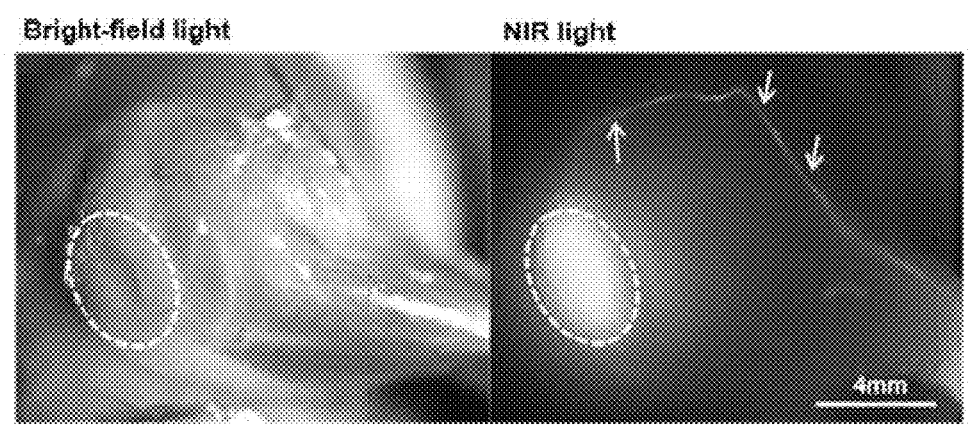

[FIG 6A]
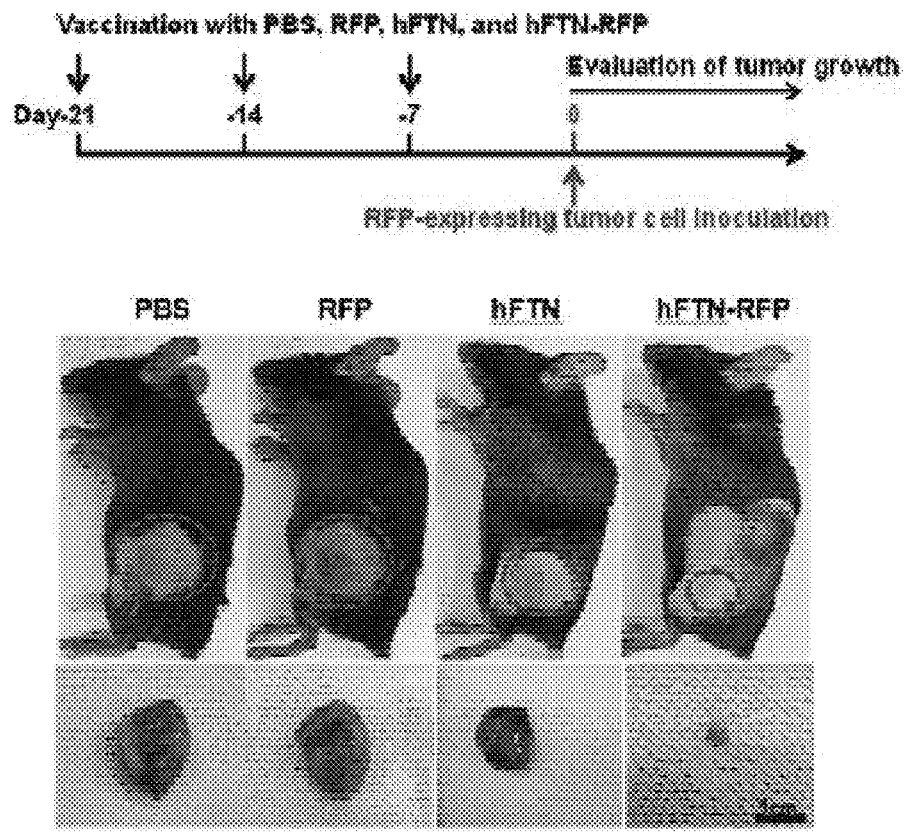
[FIG 6B]
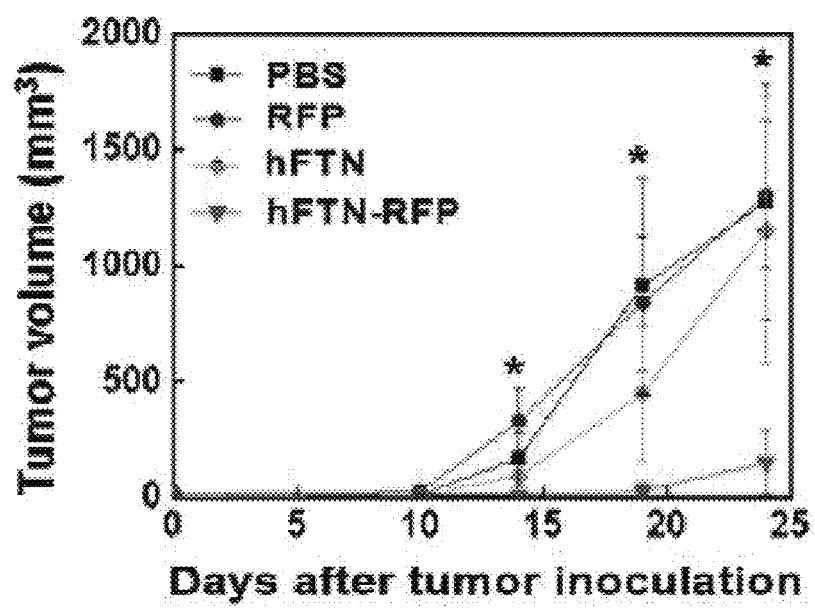

[FIG 7]
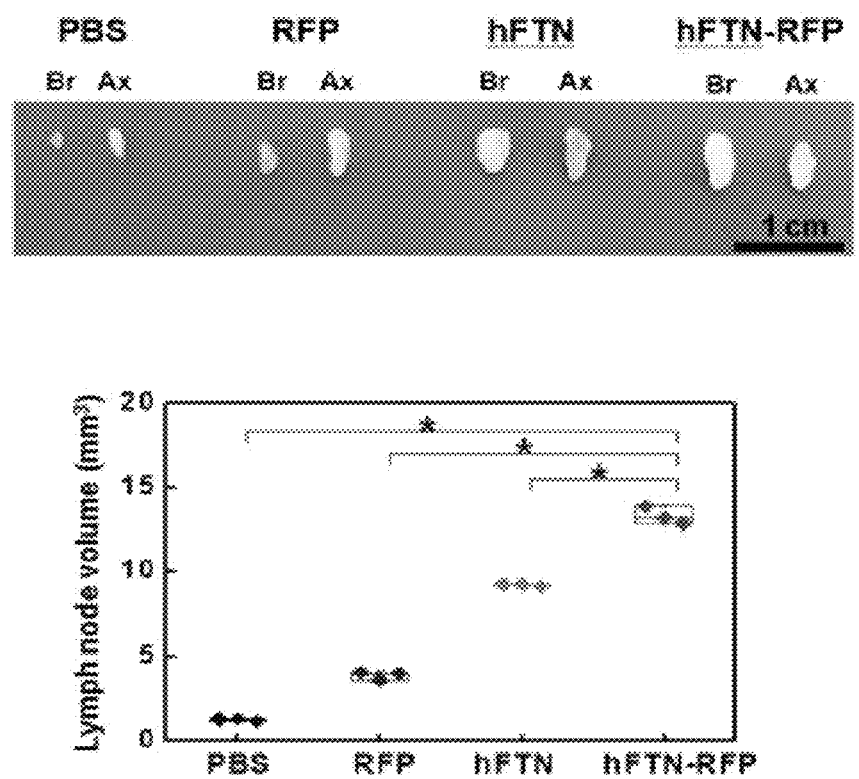

[FIG 8A]
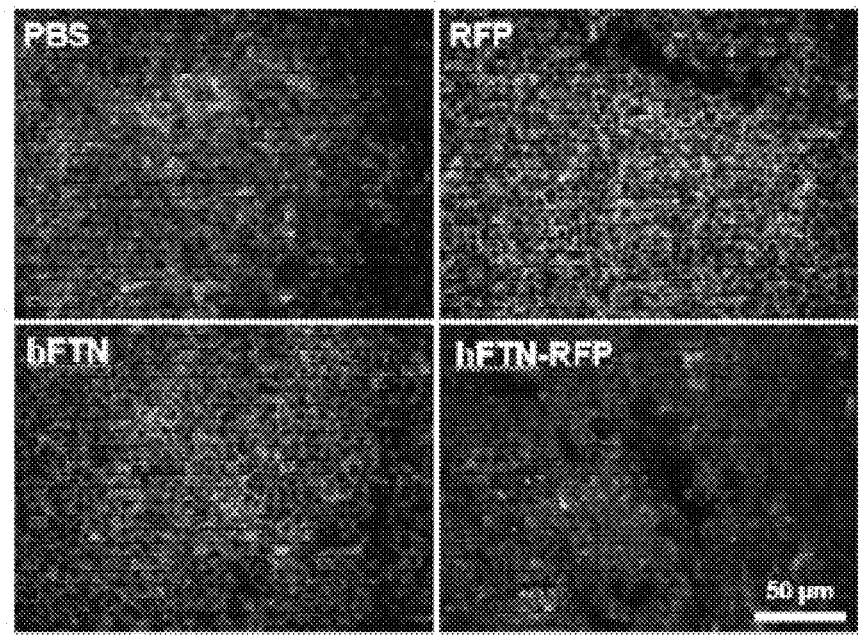
[FIG 8B]
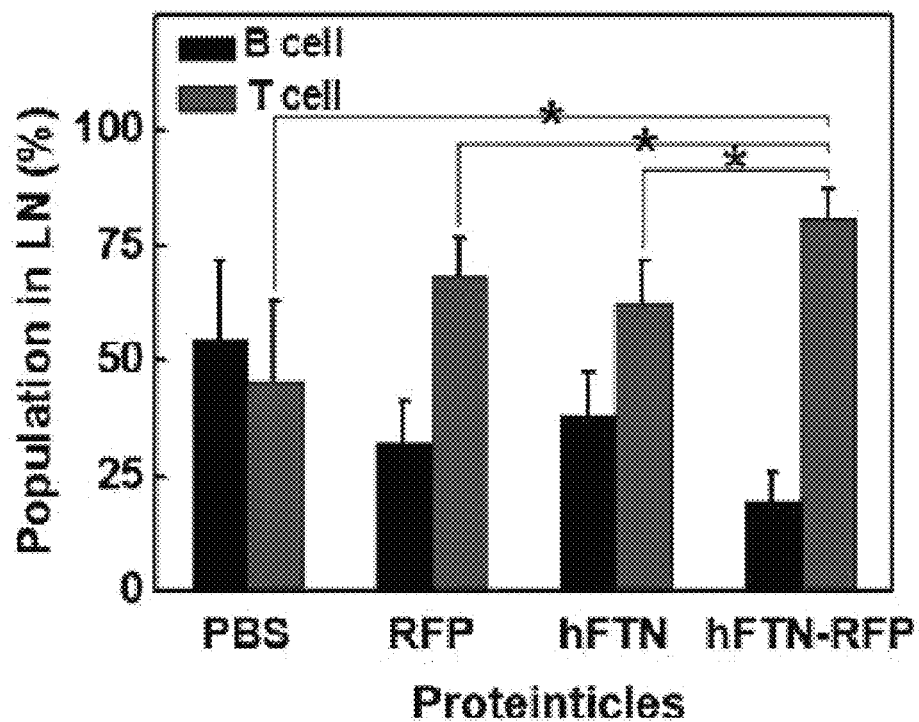

【FIG 9A】
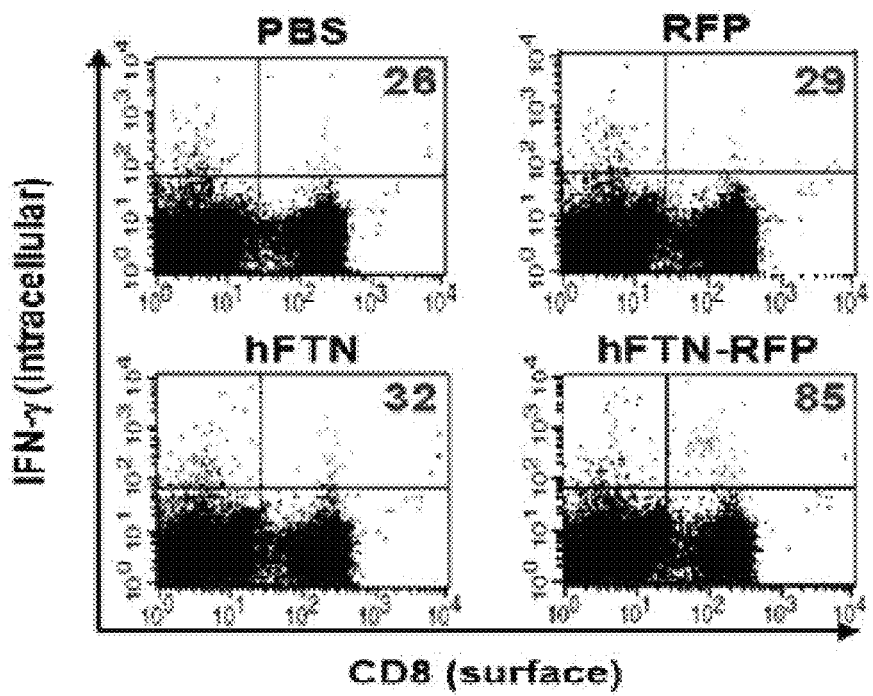
【FIG 9B】
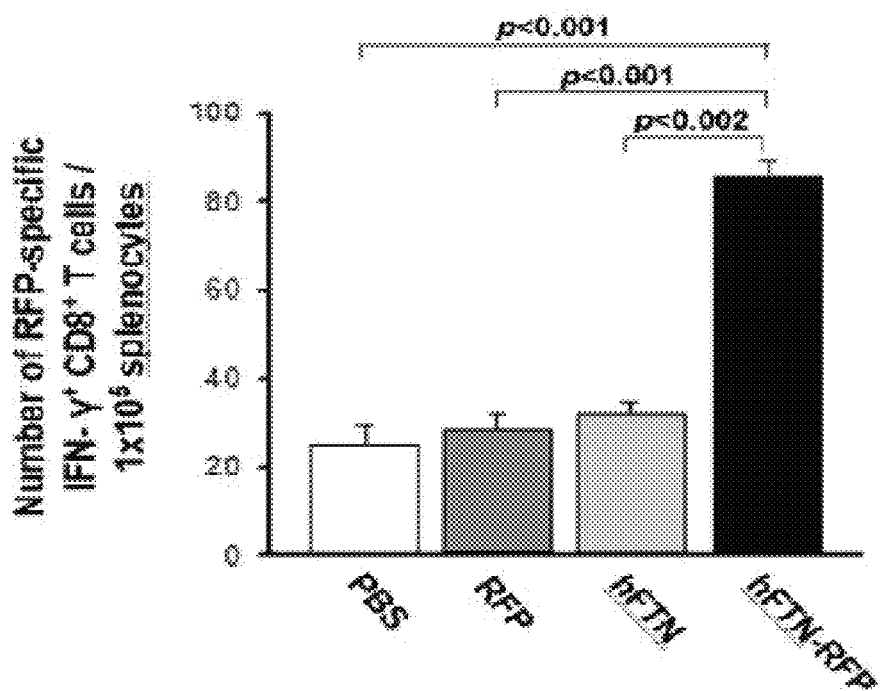

[FIG 10]
1) C-term
2) D-E domain
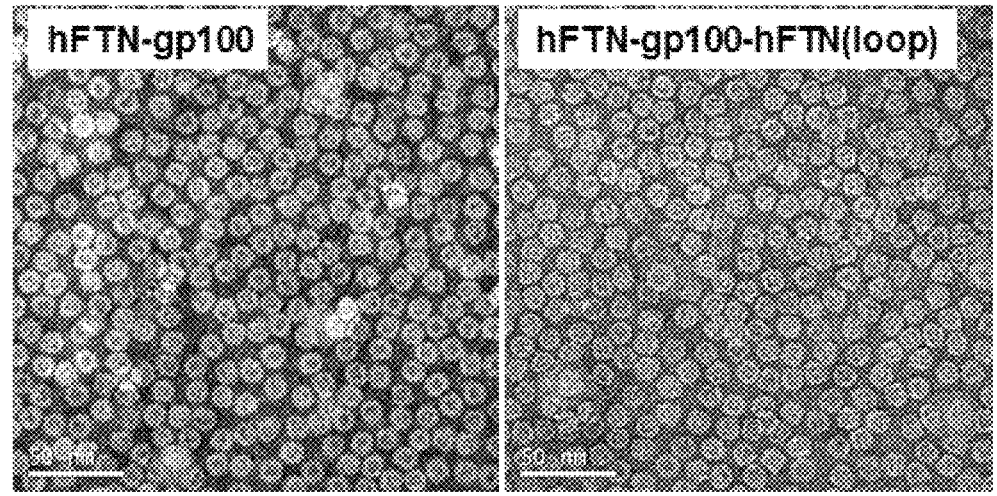

[FIG 11]
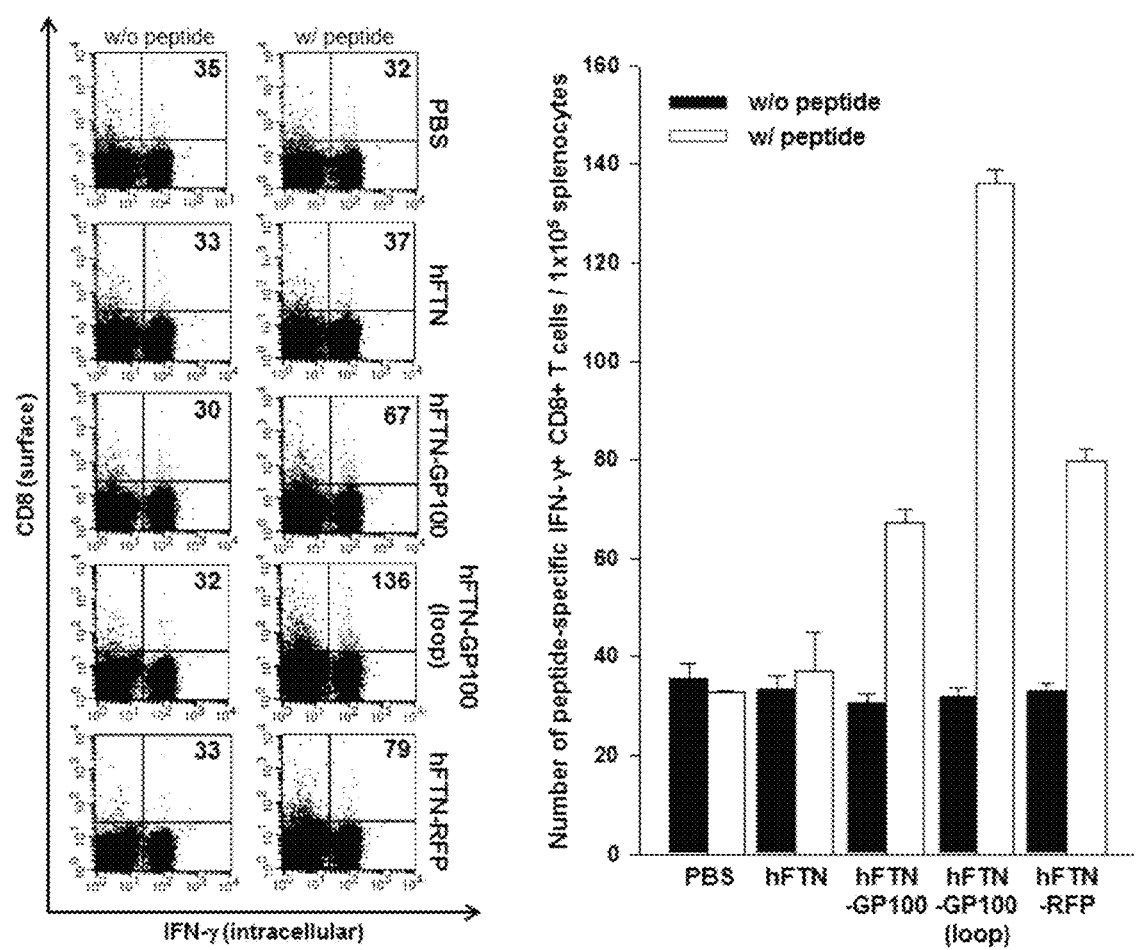

PROTEIN NANOPARTICLE LINKED WITH CANCER SPECIFIC EPITOPE AND COMPOSITION FOR CANCER IMMUNOTHERAPY COMPRISING THE SAME

CROSS-REFERENCE TO RELATED APPLICATIONS

This application claims priority under 35 U.S.C. § 119 of Korean Patent Application No. 10-2015-0147592 filed Oct. 22, 2015. The disclosure of such Korean priority patent application is hereby incorporated herein by reference in its entirety, for all purposes.

TECHNICAL FIELD

The present invention relates to a protein nanoparticle linked with a cancer specific epitope and a composition for cancer immunotherapy including the same, and more specifically, to a recombinant microorganism into which a vector in which a promoter, a gene of a human ferritin heavy chain protein, and a gene encoding a disease marker-specific epitope are operably linked is introduced, a protein nanoparticle in which a cancer-specific epitope is fused and expressed on a surface of the human ferritin heavy chain protein, a method of producing the protein nanoparticle, and a composition for cancer immunotherapy including the same, wherein the composition for cancer immunotherapy including the protein nanoparticle according to the present invention is structurally stable, and has no toxicity in the body, which is significantly useful for cancer immunotherapy.

BACKGROUND ART

In a modern society, a number of diseases are able to be easily cured, and there are few incurable diseases. However, cancer requires very difficult and complex therapies unlike treatments for other diseases, and even the complex therapies are not fully effective. Currently, a method used for cancer therapy is largely divided into surgery, radiation therapy, and chemotherapy. Cancer patients receive surgery to remove cancers, wherein when the cancer does not spread far but is only localized, the cancer is able to be completely cured only by the surgery. However, it tends to cause cancer metastasis in over 70% of patients, and thus, adjuvant therapies are accompanied with the surgery. As one of the adjuvant therapies, radiation therapy is a therapy that kills cancer cells by using high-energy radiation. When the cancer cells are treated with radiation, the radiation therapy is not able to immediately kill the cancer cells, but destroys a proliferation function of the cancer cells, thereby preventing production of new cancer cells and further division. However, this method has an adverse effect since it affects normal cells as well as the cancer cells. Chemotherapy is also an adjuvant therapy that kills the cancer cells using medicine after surgery, and is performed to kill invisible cancer cells. However, chemotherapy may also have side effects such as vomiting, diarrhea, hair loss, etc.

In order to minimize these adverse side effects, immunotherapy has emerged in recent years. Further, as described above, since the cancer metastasis rate is over 70% of total patients, it is considered that treatment of metastatic cancer is essential in completely curing the cancer, and thus, immunotherapy is a very effective treatment method.

The immunotherapy is a method of treating the cancer by using an immune response in the patient's body. The immunotherapy method may eventually achieve cancer prevention. The cancer immunotherapy is a method in which an antigen which is a cause of cancer is administered to activate cancer-specific immune cells, and then, the activated immune cells specifically attack the cancer in the body, thereby inducing treatment according to a principle of vaccines. Further, when the cancer-specific antigen is administered in a patient's body that does not suffer from cancer, the immune cells that were not activated become activated to be cancer-specific immune memory cells, and when the patient suffers from the cancer, the cells specifically attack the cancer cells.

For cancer immunotherapy, it is important to transport the cancer-specific antigen to a lymph node in which the immune cells are concentrated. Further, since a material needs to be injected into the body, toxicity in the body should be considered.

However, the existing attempts to transport only the cancer-specific antigen itself to the lymph node have not been significantly effective. The reason is that a strong immune response is not generated in the body due to a short length of cancer-specific antigen peptide (Xu, Z. et al., J. Control. Release Vol. 172, pp. 259-265, 2011; Jewel, C. M., et al., Proc. Natl. Acad. Sci. USA Vo. 108, 15745-15750, 2011).

Further, polymers have been widely used as an in vivo carrier of the cancer-specific antigen, and when cancer antigen is immobilized onto a surface of the polymer for in vivo transportation of the antigen, it needs to expose the cancer-specific antigen onto a particle surface by using a chemical bond. However, this method of using the polymer has a limitation in uniformly exposing the antigen with high density.

Ferritin is formed of 24 identical protein subunits consisting of heavy chains and light chains, and forms a hollow shell in a living body. The protein binding to iron has an iron storage function, and an iron detoxification function (Harrison et al., Biochim Biophys Acta., 1275(3): 161-163, 1996). The protein maintains iron balance in cells for growth and survival of most tissues, and functions as a cell protective protein that minimizes formation of oxygen-free radical due to the binding with the iron in the cells (Lawson et al., Nature, 349: 541-544, 1991). The ferritin has a molecular weight of about 500,000 Da, consists of heavy chains and light chains, and has a self-assembly capability to show unique property in which spherical particles are formed.

Therefore, the present inventors made an effort to develop a method of effectively transporting a cancer-specific antigen to a lymph node, and as a result, found that when an expression vector encoding a human ferritin protein monomer fused with a cancer-specific epitope was designed and produced, and expressed in *E. coli*, a protein nanoparticle in which the cancer-specific epitope was expressed on a surface of the protein nanoparticle was developed, the protein nanoparticle had a remarkable lymph node targeting capability, and also had a remarkable effect for cancer immunotherapy due to the lymph node targeting capability, as compared to the existing nanoparticles, and completed the present invention.

DISCLOSURE

Technical Problem

An object of the present invention is to provide a recombinant microorganism into which a vector in which a gene of a human ferritin heavy chain protein, and a gene encoding a cancer-specific epitope are operably linked is introduced.

Another object of the present invention is to provide a protein nanoparticle in which a disease marker-specific epitope is fused and expressed on a surface of the human ferritin heavy chain protein, and a method of producing the protein nanoparticle.

Still another object of the present invention is to provide a composition for cancer immunotherapy including the protein nanoparticle produced by the production method.

Technical Solution

In order to achieve the foregoing objects, the present invention provides a recombinant microorganism into which a vector in which a promoter, a gene of a human ferritin heavy chain protein, and a gene encoding a cancer-specific epitope are operably linked is introduced.

In addition, the present invention provides a protein nanoparticle in which a cancer-specific epitope is fused and expressed on a surface of human ferritin heavy chain protein.

Further, the present invention provides a method of producing a protein nanoparticle in which a cancer-specific epitope is expressed on a ferritin surface, including: producing the protein nanoparticle in which the cancer-specific epitope is expressed on a surface of a ferritin protein nanoparticle by culturing the recombinant microorganism as described above; and recovering the produced protein nanoparticle.

In addition, the present invention provides a composition for cancer immunotherapy including the protein nanoparticle in which the cancer-specific epitope is fused and expressed on the surface of the human ferritin heavy chain protein as an active ingredient.

DESCRIPTION OF DRAWINGS

FIG. 1 is an overall schematic diagram of protein nanoparticles for cancer immunotherapy based on lymph node targeting and vaccine platform (top panel), which shows that a human ferritin heavy chain (hereinafter, referred to as hFTN) was the most excellent by measuring a lymph node targeting efficiency among e. coli DPS (hereinafter, referred to as eDPS), the hFTN, T. acidophilum proteasome (hereinafter, referred to as tPTS), and hepatitis B virus core antigen (hereinafter, referred to as HBVC), and shows that activated immune cells attack cancer cells using the above discovery, and is TEM images observed after four kinds of nanoparticles were produced (bottom panel).

FIG. 2 is in vivo near infrared fluorescence images obtained by injecting DPS, PTS, HBVC and hFTN that are candidate nanoparticles into a C57BL/6 mouse, and then, observing lymph node targeting for 1 hour.

FIG. 3A is near infrared fluorescence images of lymph node targeting of the candidate nanoparticles such as those shown in FIG. 2, observed for a long period of time (1 min, 1 hour, 4 hours, 6 hours, one day, 3 days, and 6 days), and FIG. 3B is a graph showing the fluorescence intensity of FIG. 3A.

FIG. 4A is images of fluorescence-labeled hFTN targeted to the lymph node of a mouse in real time, and FIG. 4B is optical images (left) of the lymph node of FIG. 4A, and is near-infrared images (right) of the lymph node of FIG. 4A.

FIG. 5A schematically shows hFTN nanoparticles having a surface on which RFP as a cancer-specific epitope is expressed (top left), schematically shows an expression vector (bottom left), and shows a TEM image of nanoparticles synthesized in E. coli using the vector, and a size of the nanoparticles measured by DLS (right), and FIG. 5B shows an optical image of the lymph node of a mouse into which the nanoparticles are injected (left) and a near-infrared image (right) of the lymph node of the mouse.

FIG. 6A shows a schedule for vaccination of PBS, RFP, hFTN, and HFTN-FRP (top panel), and a cancer size measured by injecting B16F10 melanoma cell expressing the RFP into the mouse after the final injection, and FIG. 6B is a graph showing the cancer size measured in FIG. 6A.

FIG. 7 is an image of the lymph node observed after immune response for each experimental group and each control group is generated (top panel), and is a graph showing the measured lymph node (bottom panel).

FIG. 8A is a double immunofluorescence image of B cell distribution and T cell distribution for each experimental group and each control group, and FIG. 8B shows distribution degree of the B cell and the T cell in the lymph node for each experimental group and each control group.

FIG. 9A shows FACS experimental results showing the number of CD8$^+$T cells that secret IFN-$\gamma$ in spleen for each experimental group and each control group, and FIG. 9B is a graph showing the measured number of cells.

FIG. 10 schematically shows an expression vector of the hFTN produced in Example 9 (top panel), and is a TEM image of the nanoparticles produced by using the expression vector (bottom panel).

FIG. 11 shows FACS experimental results showing the number of CD8+T cells that secret IFN-$\gamma$ in the spleen for each experimental group and each control group (left panel), and shows a graph showing the measured number of cells (right panel).

BEST MODE

As far as it is not defined in other ways, all technical and scientific terms used in the present specification have the same meaning as being generally appreciated by those skilled in the art to which the present invention pertains. In general, a nomenclature used in the present specification is well known in technical fields and generally used.

In the present invention, it was attempted to confirm easiness of mass production of protein nanoparticles capable of effectively delivering a cancer-specific epitope to a lymph node, uniform particle size distribution, easiness and stability of controlling density/structure/direction of the epitope, and to confirm a cancer immunotherapeutic effect of a composition for cancer immunotherapy including the protein nanoparticle.

In order to select an appropriate cancer antigen carrier to be used for cancer immunotherapy in the present invention, lymph node targeting was performed by using e. coli DPS (hereinafter, referred to as eDPS), human Ferritin heavy chain (hereinafter, referred to as hFTN), T. acidophilum proteasome (hereinafter, referred to as tPTS), and hepatitis B virus core antigen (hereinafter, referred to as HBVC) each having a size of 10 to 80 nm and being able to pass through lymph vessels to be delivered to the lymph node. As a result, it was confirmed that hFTN was specifically bound to a TIM2-receptor of a B-cell which is an immune cell, thereby having an excellent lymph node targeting capability as compared to other particles (FIGS. 1 to 4A-4B), and that a nanoparticle manufactured so that the cancer-specific epitope was expressed on a surface of the hFTN was delivered with high efficiency to the lymph node (FIGS. 5A-5B), and that a tumor size was reduced by cancer immunotherapy using the hTFN nanoparticles having the surface on which the cancer-specific epitope was expressed in vivo (FIGS. 6A-6B to 9A-9B).

Specifically, in an exemplary embodiment of the present invention, the easiness of mass production of the protein nanoparticles in which the cancer-specific epitope was fused and expressed on a surface of the nanoparticle, the uniform particle size distribution, the easiness and the stability of controlling density/structure/direction of the epitope could be confirmed.

Accordingly, in an aspect, the present invention relates to a recombinant microorganism into which a vector in which a promoter, a gene of a human ferritin heavy chain protein, and a gene encoding a cancer-specific epitope are operably linked is introduced.

The human ferritin is a protein nanoparticle produced by self-assembly in cells with 4-3-2 symmetry phase using 24 ferritin monomers consisting of heavy chains (21 kDa) and light chains (19 kDa), and a human heavy chain ferritin monomer is bio-synthesized with a high expression rate and acceptance even in *E. coli* cells, and forms a nanoparticle having about 12 nm diameter by the self-assembly property. An activated form of human heavy chain ferritin forming the nanoparticles has structural flexibility in which N-terminal is expressed to the outside of the particle, and C-terminal is capable of being easily expressed to the outside of the particle when it is fused to a heterologous protein or peptide, and thus, if a peptide or a protein having a detection probe function is fused to the N-terminal or the C-terminal using a gene recombination technology, surface properties of the ferritin nanoparticle are able to be modified.

In the present invention, the promoter may be selected from the group consisting of trc promoter, tac promoter, T7 promoter, lac promoter, trp promoter, $P_L(\lambda)$ promoter, $P_R(\lambda)$ promoter, lac(TS) promoter, $P_{SPA}$ promoter, ibpfxs promoter, groES promoter, groEL promoter, clpB promoter, dnaK promoter, and dnaJ promoter.

In the present invention, the microorganism may be selected from the group consisting of *Bacillus* sp., *Corynebacterium* sp., *Escherichia* sp., *Pichia* sp., *Pseudomonas* sp., and *Saccharomyces* sp.

In the present invention, in the vector, a linker sequence is further operably linked between the human ferritin heavy chain protein and the cancer-specific epitope.

In the present invention, the linker sequence is not limited as long as it is a sequence for increasing a surface expression property of the protein nanoparticle by providing flexibility to the epitope, and the linker sequence is, for example, $G_3SG_3TG_3SG_3$ (SEQ ID NO: 2).

In the present invention, the cancer may be a solid tumor, and preferably, may be selected from the group consisting of liver cancer, gliocytoma, ovarian cancer, colon cancer, head and neck cancer, bladder cancer, renal cell cancer, gastric cancer, breast cancer, metastatic cancer, prostate cancer, pancreatic cancer, skin cancer, melanoma, and lung cancer.

In the present invention, the cancer-specific epitope is any tumor antigen as long as it is capable of binding with a dendritic cell (DC) in the lymph node in vivo to activate the DC into an antigen-presenting cell (APC), and for example, may be an epitope selected from the group consisting of melanoma B16F10 antigen, gp100 peptide, and lymphoma cell line EL4 antigen, and may be represented by SEQ ID NO: 1.

The present invention also provides a protein nanoparticle in which a cancer-specific epitope is fused and expressed on a surface of human ferritin heavy chain protein.

In the present invention, the functional protein nanoparticle has a diameter of 10 to 40 nm.

In the present invention, the cancer may be a solid tumor, and preferably, may be selected from the group consisting of liver cancer, gliocytoma, ovarian cancer, colon cancer, head and neck cancer, bladder cancer, renal cell cancer, gastric cancer, breast cancer, metastatic cancer, prostate cancer, pancreatic cancer, skin cancer, melanoma, and lung cancer.

In the present invention, the cancer-specific epitope is any tumor antigen as long as it is capable of binding with a dendritic cell (DC) in the lymph node in vivo to activate the DC into an antigen-presenting cell (APC), and for example, may be an epitope selected from the group consisting of melanoma B16F10 antigen, gp100 peptide, and lymphoma cell line EL4 antigen, and may be represented by SEQ ID NO: 1.

Further, the present invention provides a method of producing a protein nanoparticle in which a cancer-specific epitope is fused and expressed on a ferritin surface, including: producing the protein nanoparticle in which the cancer-specific epitope is expressed on a surface of a ferritin protein nanoparticle by culturing the recombinant microorganism as described above; and recovering the produced protein nanoparticle. The production method is effective in view of cost since it uses a microorganism, and it is possible to mass-produce the protein nanoparticle.

Further, the protein nanoparticle of the present invention may express two or more of the cancer-specific epitopes on the surface at various rates by changing the intensity of the promoter. For example, the nanoparticle of the present invention may be produced by the method of producing the protein nanoparticle, the method including: culturing a recombinant microorganism into which a first vector in which a strong or weak promoter, a gene of a human ferritin heavy chain protein, and a gene encoding a cancer-specific epitope are operably linked; and a second vector in which a strong or weak promoter, a gene of a human ferritin heavy chain protein, and a gene encoding a cancer-specific epitope are operably linked (provided that the promoters and the genes encoding the disease marker-specific epitope between the first and second vectors are different) are introduced to produce the protein nanoparticles having a surface on which different cancer-specific epitopes are expressed; and recovering the protein nanoparticles. The strong promoter may be selected from the group consisting of trc promoter, tac promoter, T7 promoter, lac promoter, trp promoter, $P_L(\lambda)$ promoter, $P_R(\lambda)$ promoter, lac(TS) promoter, $P_{SPA}$ promoter, and the weak promoter may be selected from the group consisting of ibpfxs promoter, groES promoter, groEL promoter, clpB promoter, dnaK promoter, and dnaJ promoter.

In the present invention, the cancer may be a solid tumor, and preferably, may be selected from the group consisting of liver cancer, gliocytoma, ovarian cancer, colon cancer, head and neck cancer, bladder cancer, renal cell cancer, gastric cancer, breast cancer, metastatic cancer, prostate cancer, pancreatic cancer, skin cancer, melanoma, and lung cancer.

In the present invention, the cancer-specific epitope is any tumor antigen as long as it is capable of binding with a dendritic cell (DC) in the lymph node in vivo to activate the DC into an antigen-presenting cell (APC), and for example, may be an epitope selected from the group consisting of melanoma B16F10 antigen, gp100 peptide, and lymphoma cell line EL4 antigen, and may be represented by SEQ ID NO: 1.

```
                                        (SEQ ID NO: 1)
            Candidate 1: KVPRNQDWL
```

Meanwhile, it was predicted that at the time of using a composition for cancer immunotherapy containing the protein nanoparticles produced in the present invention as the active ingredient, the cancer immunotherapy was able to be effectively achieved.

Specifically, in another exemplary embodiment of the present invention, it was found that PBS, RFP, hFTN, and hFTN-FRP were injected three times into a mouse at 1 week interval, followed by injection with B16F10 melanoma cell expressing RFP into the mouse, and the cancer size was measured, and as a result, the melanoma size was dramatically reduced in the mouse injected with hFTN-RFP (FIGS. 6A-6B), and the immune responses in the experimental group and the control group were measured, and as a result, the immune response was the most actively generated in the group injected with hFTN-RFP (FIGS. 9A-9B).

Therefore, in another aspect, the present invention relates to a composition for cancer immunotherapy including the protein nanoparticle in which the cancer-specific epitope is fused and expressed on the surface of the human ferritin heavy chain protein as an active ingredient.

The composition for cancer immunotherapy including the protein nanoparticle according to the present invention may further include a pharmaceutically acceptable carrier, and may be formulated together with the carrier.

The phrase used herein "the pharmaceutically acceptable carrier" means a carrier or a diluent that does not inhibit biological activity and properties of the administered compound without stimulating organisms. The pharmaceutically acceptable carrier in the composition to be formulated as a liquid solution is sterilized and is suitable for a living body. As the carrier, saline, sterile water, Ringer's solution, buffered saline, albumin injection solution, dextrose solution, maltodextrin solution, glycerol, and ethanol may be used, or at least one component thereof may be mixed to be used, and other conventional additives such as an antioxidant, buffer, a bacteriostatic agent, etc., may be added as needed. In addition, the composition may be prepared into formulations for injection, such as an aqueous solution, suspension, emulsion, etc., pill, a capsule, a granule or a tablet by further adding diluent, dispersant, surfactant, binder and lubricant thereto.

The composition for cancer immunotherapy including the protein nanoparticle and the pharmaceutically acceptable carrier is applicable to any formulation including the composition as an active ingredient, and may be prepared as oral or parenteral formulation. The pharmaceutical formulation of the present invention includes forms appropriate for oral administration, rectal administration, nasal administration, topical administration (including cheek and sublingual), subcutaneous administration, vaginal or parenteral administration (including intramuscular, subcutaneous, and intravenous administration) or forms appropriate for administration by inhalation or insufflation.

The formulation for oral administration including the composition of the present invention as the active ingredient may be, for example, tablets, troches, lozenge, aqueous or oil suspensions, prepared powders or granules, emulsions, hard or soft capsules, syrups or elixirs. For preparing the formulation of tablets, capsules, etc., a binder such as lactose, saccharose, sorbitol, mannitol, starch, amylopectin, cellulose or gelatin, an excipient such as dicalcium phosphate, a disintegrating agent such as corn starch or sweet potato starch, a lubricant such as magnesium stearate, calcium stearate, sodium stearyl fumarate or polyethyleneglycol wax, may be included, and a capsule formulation may further contain a liquid carrier such as fatty oil in addition to the above-described materials.

The formulation for parenteral administration including the composition of the present invention as an active ingredient may include an injectable form such as subcutaneous injection, intravenous injection, intramuscular injection, or the like, suppository injection, and a spray form such as an aerosol that induces inhalation through a respiratory tract, or the like. For the injectable formulation, the composition of the present invention may be mixed in water with a stabilizer or a buffer to prepare a solution or a suspension, and the prepared solution or suspension may be formulated for unit dose of ampoules or vials. For the suppository injection, a composition for rectal administration such as a suppository or an enema including general suppository base such as cocoa butter, other glycerides, or the like, may be formulated. For the spray formulation such as the aerosol, etc., a propellant, etc., may be blended with additive so that water-dispersed concentrate or wet powder is dispersed.

As another embodiment, the present invention relates to a method of treating cancer including administering a composition for cancer immunotherapy, the composition including the protein nanoparticles.

The term used herein "administration" means introduction of the pharmaceutical composition of the present invention to a patient by any appropriate method. An administration route of the composition of the present invention may be various oral or parenteral routes as long as the composition is able to reach a target tissue, and specifically, the composition may be administered in a conventional manner through oral, rectal, topical, intravenous, intraperitoneal, intramuscular, intraarterial, transdermal, nasal, inhalation, intraocular, or intradermal route.

The treatment method of the present invention includes administering a pharmaceutically effective amount of the composition for cancer immunotherapy of the present invention. It is obvious for those skilled in the art that physician may determine a suitable total daily usage within a correct range of medical judgment. It is preferred that the specific therapeutically effective amount for a particular patient varies depending on type and degree of a reaction to be achieved, specific composition including whether other agents are used according to cases, patient's age, body weight, general health status, sex and diet, administration time, administration route, a secretion rate of the composition, a treatment duration, and various factors including drugs used together with or simultaneously used with the specific composition, and similar factors well-known in a medical field. Therefore, the effective amount of the composition for preventing or treating cancer that is suitable for the purposes of the present invention is preferably determined in consideration of the above-mentioned factors.

In addition, the treatment method of the present invention is applicable to any animal in which the dendritic cell recognizes the antigen in the lymph node to be activated into the antigen-presenting cell (APC), thereby causing an immune response, wherein the animal includes livestock such as cows, pigs, sheep, horses, dogs, cats, etc., as well as human and primates.

Hereinafter, the present invention will be described in more detail with reference to the following Examples. However, the following Examples are only for exemplifying the present invention, and it will be obvious to those skilled in the art that the scope of the present invention is not construed to be limited to these Examples.

EXAMPLE 1

Production of Expression Vector for Synthesizing Candidate Protein Nanoparticles Protein nanoparticles, DPS, PTS, HBVC, hFTN, and hFTN-RFP, were produced by PCR according to Table 1 showing vectors. All of the produced plasmid expression vector was purified in the agarose gel, and then, sequences were confirmed through complete DNA sequencing.

The PCR products as obtained above were sequentially inserted into pT7-7 or pET28a vector to constitute the expression vectors capable of expressing the respective protein nanoparticles.

The vectors for expressing the respective protein nanoparticles were pT7-DPS, pT7-PTSβ, pET28a-PTSα, pET28a-HBVC, pT7-FTN, and pT7-FTN:RFP.

TABLE 1

Vector composition for each nanoparticle

| Protein nanoparticle | Expresstion vector |
|---|---|
| DPS | $NH_2$-NdeI-$(His)_6$-DPS-HindIII-COOH wherein the hexapetide chain $(His)_6$ is SEQ ID NO: 3 |
| PTS | $NH_2$-NdeI-PTSα-HindIII-COOH, $NH_2$-NdeI-PTSβ-$(His)_6$-HindIII-COOH wherein the hexapeptide chain $(His)_6$ is SEQ ID NO: 3 |
| HBVC | $NH_2$-NdeI-HBVC-HindIII-COOH |
| hFTN | $NH_2$-NdeI-$(His)_6$-hFTN-HindIII-COOH wherein the hexapetide chain $(His)_6$ is SEQ ID NO: 3 |
| hFTN-RFP | $NH_2$-NdeI-$(His)_6$-hFTN-XhoI-linker(G3SG3TG3SG3)-RFP-HindIII-COOH wherein the hexapetide chain $(His)_6$ is SEQ ID NO: 3, and wherein the linker (G3SG3TG3SG3) is SEQ ID NO: 2 |

EXAMPLE 2

Biosynthesis of Candidate Protein Nanoparticles

E. coli strains BL21(DE3)[F-ompThsdSB(rB-mB-)] were transformed with the produced expression vectors, respectively, and ampicillin-resistant transformants were selected. The transformed E. coli strains were cultured in 250 mL Erlenmeyer flasks (37° C., 150 rpm) containing 50 mL Luria-Bertani (LB) medium (containing 100 mg of L-1 ampicillin) When medium turbidity (O.D 600) reached about 0.5 to 0.7, IPTG (isopropyl-β-D-thiogalactopyranoside) (1.0 mM) was injected to induce expression of recombinant genes. After culturing the genes for 16 to 18 hours at 20° C., the cultured E. coli strains were centrifuged at 4,500 rpm for 10 minutes to collect cell sediments, and the cell sediments were suspended in 5 ml disruption solution (10 mM Tris-HCl buffer, pH 7.5, 10 mM EDTA) and disrupted using an ultrasonic disruptor (Branson Ultrasonics Corp., Danbury, Conn., USA). After disruption, the products were centrifuged at 13,000 rpm for 10 minutes, and the supernatant was separated from insoluble aggregate. The separated supernatant was used for next experiment.

EXAMPLE 3

Purification of hFTN-RFP Protein Nanoparticle and Attachment Fluorescent Substance The supernatant obtained in Example 2 was purified through the following 3 steps. First, 1) the recombinant protein was subjected to Ni2+-NTA affinity chromatography using a combination of fusion-expressed histidine and nickel, 2) the recombinant protein was concentrated and a fluorescent substance was attached thereto through buffer exchange, and lastly, 3) sucrose gradient ultracentrifugation was performed to separate only self-assembled protein nanoparticles to which the fluorescent substance was attached. Each step is detailed described as follows.

1) Ni2+-NTA Affinity Chromatography

In order to purify the recombinant protein, E. coli cultured by the same method as described above was recovered, and cell pellets thereof were re-suspended in 5 mL lysis buffer (pH 8.0, 50 mM sodium phosphate, 300 mM NaCl, 20 mM imidazole), and the cells were disrupted using the ultrasonic disruptor. The disrupted cell solution was centrifuged at 13,000 rpm for 10 minutes to separate only the supernatant, and then, each recombinant protein was separated using Ni2+-NTA column (Qiagen, Hilden, Germany) (washing buffer: pH 8.0, 50 mM sodium phosphate, 300 mM NaCl, 80 mM imidazole/elution buffer: pH 8.0, 50 mM sodium phosphate, 300 mM NaCl, 200 mM imidazole).

2) Concentration and Buffer Exchange and Attachment of Fluorescent Substance 3 ml of the recombinant protein eluted through Ni2+-NTA affinity chromatography was placed in a ultracentrifugal filter (Amicon Ultra 100K, Millipore, Billerica, Mass.) and centrifuged with 5,000 g until the solution was left in an amount of 1 ml on the column. Then, in order to attach NIR fluorescent substance, cy5.5, the protein particle was subjected to buffer-exchange with a sodium bicarbonate (0.1 M, pH 8.5) buffer, and the fluorescent substance was attached for 12 hours at room temperature.

3) Sucrose Gradient High-Speed Centrifugation

Sucrose each having different concentration was added to PBS (2.7 mM KCl, 137 mM NaCl, 2 mM $KH_2PO_4$, 10 mM $Na_2HPO_4$, pH 7.4) buffer to prepare solutions each containing 40%, 35%, 30%, 25%, and 20% sucrose, and then, the sucrose solutions each having an amount of 2 mL with different concentration (45 to 20%) were put in a high-speed centrifugation tube (ultraclear 13.2 ml tube, Beckman) sequentially from the solution with the highest concentration, and then, the tube was filled with 1 ml of the recombinant protein solution present in a prepared buffer for self-assembly, followed by high-speed centrifugation at 35,000 rpm and 4° C. for 16 hours (Ultracentrifuge L-90k, Beckman) After the centrifugation, the top layer (20-25% sucrose solution part) was subjected to buffer-exchange of the recombinant protein with the ultracentrifugal filter and PBS buffer as defined in 2) above using a pipette carefully.

EXAMPLE 4

NIR Image Analysis Using Produced Protein Nanoparticle

The fluorescence of the five protein nanoparticles produced in Example 3 above was regulated, and the protein nanoparticles were injected into five-week-old nude mouse, and a substance having the most excellent targeting efficiency in the lymph node among the DPS, PTS, HBVC, and hFTN was selected, and comparison was conducted to confirm whether the hFTN-RFP particle actually had the excellent lymph node targeting efficiency as compared to other particles. 20 μl of the respective particles were injected into right foot of the mouse, and targeting aspects of the four DPS, PTS, HBVC, and hFTN particles until the particles were escaped from the body for 6 days were observed by using Kodak image station (4000 MM; Kodak, New Haven, Conn.) provided with Cy5.5 bandpass emission filter and special C-mount lens or IVIS spectrum imaging system (Caliper Life Sciences, Hopkinton, Mass.), and as a result, it was confirmed that the hFTN had the highest lymph node targeting efficiency, and the lymph node targeting was more excellent in the hFTN-RFP particles as compared to a case where only the RFP antigen was injected (FIGS. 2 to 4A-4B).

EXAMPLE 5

Verification of Protein Particle Assembly

For the structure analysis of the purified recombinant protein nanoparticles of the respective protein nanoparticles produced in Example 3, the recombinant proteins were taken by transmission electron microscope (TEM). First, the unstained and purified protein samples were placed on carbon-coated copper electron microscope grids, and were naturally dried. In order to obtain stained images of the protein nanoparticles, the electron microscope grids including the naturally dried samples together with 2% (w/v) aqueous uranyl acetate solution were incubated at room temperature for 10 minutes and washed with distilled water three to four times. The protein nanoparticle images were observed by Philips Technai 120 kV electron microscope, and as a result, it was confirmed that the respective particles form spherical or cylindrical nanoparticles (FIG. 5A).

EXAMPLE 6

Tissue Experiment for Lymph Node Analysis

Control group, i.e., PBS (buffer), RFP, hFTN, and hFTN-RFP particles without the fluorescent substance were produced by methods of Examples 1 to 3, followed by vaccine injections three times at 1 week interval into the C57BL/6 mouse in which the immune response was inducible, thereby inducing boosting of the immune cells in the body, and then, it was confirmed whether the immune cells in the lymph node were actually activated into T cell capable of conducting cancer cell necrosis as follows.

First, the lymph node of each mouse was separated and observed, and as a result, it was confirmed that a size of the lymph node of the mouse injected with hFTN-RFP was the biggest (FIG. 7). Then, a lymph node tissue of the mouse injected with the respective particles was immobilized to a slide glass having a thickness of 5 μm, followed by reaction with monoclonal mouse anti human CD79α (1:200 diluted in PBS; DakoCytomation, Carpinteria, Calif.) for 2 hours, and FITC (fluorescein isothiocyanate)-labeled goat anti-mouse IgG2b (1:300 diluted in PBS; Santa Cruz Biotechnology, Santa Cruz, Calif.) for 40 minutes for B cell detection, and for T cell detection, followed with polyclonal rabbit anti-human CD3 (1:200 diluted in PBS; DakoCytomation) and CFL555-labeled mouse anti-rabbit IgG (1:300 diluted in PBS; Santa Cruz biotechnology), and observation with IX81-ZDC focus drift compensation microscope, and as a result, it was confirmed that T cell distribution was the highest in the mouse injected with hFTN-RFP (FIGS. 8A-8B).

EXAMPLE 7

Experiment for Confirming Secretion of Specific Cytokine Through CD8+ T Cell Assay PBS (buffer) and RFP, hFTN, and hFTN-RFP particles were produced by methods of Examples 1 to 3, followed by vaccine injections three times into the C57BL/6 mouse at 1 week interval to induce immune response boosting of immune cells in the lymph node, and spleen in which the immune cells were collected was extracted and crushed. Next, CD8+T cells in which immune response was cancer-specifically induced in RFP model cancer antigen were extracted in the crushed spleen, and reacted with a specific part of antigen peptide (S111 to 1119 or SSLQDGCFI) (SEQ ID NO: 4) of RFP known to generate the immune response in vitro to confirm whether RFP-specific cytokine was secreted, and as a result, it was confirmed that the CD8+T cell extracted from the spleen of the mouse injected with hFTN-RFP secreted the largest amount of cytokine (FIGS. 9A-9B).

EXAMPLE 8

Experiment to Confirm Whether Cancer Growth is Inhibited

The C57BL/6 mice were injected with samples containing hFTN-RFP (10 μM), hFTN (10 μM), RFP (10 μM) proteins and PBS buffer only three times at 1 week interval, respectively, and maintained for 1 week so as to generate the immune response. Then, the RFP-B16F10 (melanoma in which the RFP antigen was expressed) was planted into each mouse, and a cancer growth rate was observed. A cancer cell size was calculated as follows. (tumor volume)=(major axis)×(minor axis)×0.52. As a result, it was confirmed that the cancer size of the mouse experimental group with hFTN-RFP injection immunotherapy was remarkably smaller than those of the control groups (FIGS. 6A-6B).

EXAMPLE 9

Construction of Vector Using Actual Specific Tumor Antigen Peptide Model and ICS Experiment A vector was constructed by inserting a gp100 peptide, specifically, 9-amino acid peptide (KVPRNQDWL) (SEQ ID NO: 1) between 25-33 that was a part known to have immunogenicity in human Melanoma Antigen gp100, into C-terminal (hFTN-gp100) and into the middle of loop (hFTN-gp100-hFTN) positioned in D-E domain among hFTN domains (Top panel in FIG. 10).

Then, the protein nanoparticles were constructed through processes of Examples 2 and 3 (bottom panel in FIG. 10), and the mouse body was vaccinated with the corresponding nanoparticles for 3 weeks, and splenocyte was extracted for intracellular cytokine staining (ICS) experiment to confirm secretion of CD 8+ T cell & cytokine in Example 7. As positive controls for confirming whether the experiment was properly conducted, the same experiment was simultaneously performed by vaccinating the mouse body with the adjuvant and the previously experimented hFTN-RFP particle for 3 weeks, and extracting the corresponding splenocyte, and results thereof were compared with the ICS experiment using the hFTN-gp100 particle and the hFTN-gp100-hFTN particle.

As a result, it was confirmed that immune boosting using the hFTN-gp100-hFTN particle was more effectively generated as compared to that of the hFTN-gp100 particle (FIG. 11).

The protein nanoparticle according to the present invention is a three-dimensional nanostructure that is naturally biosynthesized in a cell, is synthesized while maintaining particle topology with an always accurate quaternary struc-

The invention claimed is:

1. A protein nanoparticle having a lymph node targeting capability in which a cancer-specific epitope is fused on human ferritin heavy chain protein, wherein the cancer-specific epitope is expressed on a surface of human ferritin heavy chain protein, wherein the cancer specific epitope is selected from the group consisting of melanoma B16F10 antigen, gp100 peptide, and lymphoma cell line EL4 antigen.

2. The protein nanoparticle of claim 1, wherein diameter of the protein nanoparticle is 10 to 40 nm.

3. The protein nanoparticle of claim 1, wherein the cancer is selected from the group consisting of liver cancer, gliocytoma, ovarian cancer, colon cancer, head and neck cancer, bladder cancer, renal cell cancer, gastric cancer, breast cancer, metastatic cancer, prostate cancer, pancreatic cancer, skin cancer, melanoma, and lung cancer.

```
                          SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: cancer-specific epitope

<400> SEQUENCE: 1

Lys Val Pro Arg Asn Gln Asp Trp Leu
1               5

<210> SEQ ID NO 2
<211> LENGTH: 15
<212> TYPE: PRT
<213> ORGANISM: Artificial Sequence
<220> FEATURE:
<223> OTHER INFORMATION: Linker sequence

<400> SEQUENCE: 2

Gly Gly Gly Ser Gly Gly Gly Thr Gly Gly Gly Ser Gly Gly Gly
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Hexapeptide chain

<400> SEQUENCE: 3

His His His His His His
1               5

<210> SEQ ID NO 4
<211> LENGTH: 9
<212> TYPE: PRT
<213> ORGANISM: Artificial Sequence
<220> FEATURE:
<223> OTHER INFORMATION: Immune response-mediating antigen peptide
      sequence

<400> SEQUENCE: 4

Ser Ser Leu Gln Asp Gly Cys Phe Ile
1               5
```

4. The protein nanoparticle of claim 1, wherein the cancer specific epitope is a tumor antigen which is capable of binding with a dendritic cell (DC) in the lymph node in vivo to activate the DC into an antigen-presenting cell (APC).

5. The protein nanoparticle of claim 1, wherein the cancer specific epitope is represented by SEQ ID NO: 1.

6. A method for cancer immunotherapy, the method comprising administering to a subject in need thereof, the protein nanoparticle having a lymph node targeting capability according to claim 1, as an active ingredient.

7. The method of claim 6, wherein the cancer is a solid tumor.

8. The method of claim 7, wherein the solid tumor is selected from the group consisting of liver cancer, gliocytoma, ovarian cancer, colon cancer, head and neck cancer, bladder cancer, renal cell cancer, gastric cancer, breast cancer, metastatic cancer, prostate cancer, pancreatic cancer, skin cancer, melanoma, and lung cancer.

9. The method of claim 6, wherein the cancer immunotherapy is occurred by activated immune-cell which is activated by the cancer-specific epitope of surface of protein nanoparticle of claim 1, wherein the protein nanoparticle is transferred to the lymph nodes.

\* \* \* \* \*